United States Patent

Bossak

[11] 3,948,257
[45] Apr. 6, 1976

[54] VULVAR DEODORANT SYSTEM

[76] Inventor: William Stephen Bossak, 727 Westbourne Drive, Apt. 305, West Hollywood, Calif. 90069

[22] Filed: Aug. 21, 1975

[21] Appl. No.: 606,384

Related U.S. Application Data

[63] Continuation-in-part of Ser. No. 514,171, Oct. 11, 1974, abandoned.

[52] U.S. Cl. ............................... 128/285; 128/270
[51] Int. Cl.² ......................................... A61F 13/20
[58] Field of Search ........ 128/285, 270, 271, 290 R, 128/263; 239/36

[56] References Cited
UNITED STATES PATENTS

| | | | |
|---|---|---|---|
| 1,683,545 | 9/1928 | Harris | 239/36 |
| 2,109,092 | 2/1938 | Roll | 239/36 |
| 3,037,506 | 6/1962 | Penska | 128/285 |
| 3,270,525 | 9/1966 | Sellers | 63/1 |
| 3,690,321 | 9/1972 | Hirshman | 128/285 |
| 3,777,755 | 12/1973 | Groves | 128/271 |
| 3,791,385 | 2/1974 | Davis | 128/263 |
| 3,815,600 | 6/1974 | Groves | 128/271 |
| 3,830,237 | 8/1974 | Bernardin | 128/270 |

*Primary Examiner*—Aldrich F. Medbery
*Attorney, Agent, or Firm*—Benoit Law Corporation

[57] ABSTRACT

A vulvar deodorant system comprises a tampon for insertion into the vagina and a device for retaining a dedorant. A string or other article is connected to the tampon and to the deodorant retaining device for suspending this retaining device and a deodorant retained thereby outside of the vagina and at a distance therefrom, when the tampon is inserted in the vagina.

17 Claims, 1 Drawing Figure

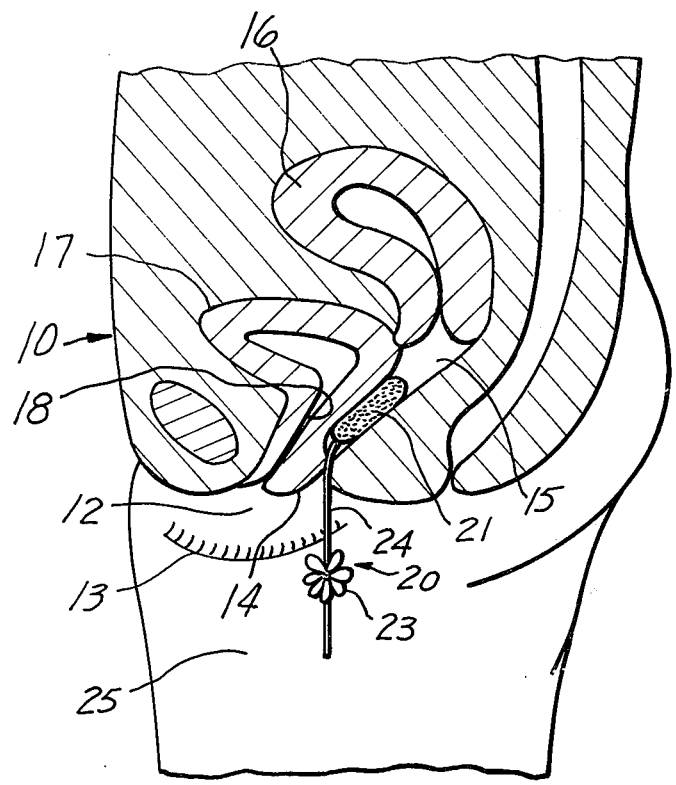

VULVAR DEODORANT SYSTEM

CROSS-REFERENCE

This is a continuation-in-part of my copending patent application Ser. No. 514,171, filed Oct. 11, 1974, and now abandoned entitled Vaginal Tampon Deodorant Tag, and herewith incorporated by reference herein.

BACKGROUND OF THE INVENTION

1. Field of the Invention

The subject invention relates to feminine hygiene articles and, more specifically, to catamenial devices and vulvar deodorant systems.

2. Description of the Prior Art

Offensive female genital odor has been a concern of many throughout the centuries. The etiologies of the malodor are multiple.

The vulva is abundant with sweat glands. Production of perspiration with subsequent decomposition, primarily by bacteria, gives rise to odorous substances such as fatty acids, ammonia, amines and hydrogen sulfide.

During menstruation, decomposition of menstrual elements, especially upon exposure to air, and the increased secretions of the vulvar sebaceous glands give rise to a characteristic odor.

Multiple gynecologic pathologic conditions produce genital ordors. Cervicitis, vaginitis and vulvitis may all cause odor. Some systemic disorders may also be a cause.

Many methods are employed to deal with female genital odor.

Perfumes are used to disguise genital odor. Inherent problems sometimes associated with the direct application of perfumes to the vulva are: Allergic hypersensitivity reactions with subsequent rash, burning and itching, all of which may predispose to infection (i.e. vulvo vaginitis); Local vaginal irritations or even systemic absorption of the perfume can occur with improper application to the membranes of the vagina; inadvertant over-application would make others acutely aware the perfume is being used.

Scented powders also present problems. The same problems discussed above in relation to perfumes can occur with powders. In addition, powders are messy, difficult to apply and tend to cake.

As with perfumes and powders, the ingredients in "feminine hygiene deodorant sprays" of the aerosol type, can cause vulvitis and vulvovaginitis. Aerosols can cause additional hazards. Ingredients which are propelled onto the vulva and/or into the vagina by the pressure of an aerosol spray are more prone to become imbedded in the vulvar skin and/or vaginal mucosa and hence are more likely to cause irritation. Aerosol propellants (fluroalkane gases) may cause cardiac toxicity when inhaled. Pressure from the propellants may be important in urethral reactions, and depending on the distance from the skin at which aerosols are discharged, effects ranging from cooling to actual freezing of the tissue may occur.

Douching used to control genital odor also may present hazards. Chemical vaginitis may develop following the introduction of incorrectly prepared douches into the vagina. Traumatic vaginitis may occur if the solution is too hot or if taken under pressure. Improper vaginal douching may lead to pelvic inflammation (vaginitis, endometritis, and salpingitis). Cases of peritonitis resulting from transuterine passage of the vaginal douche fluid have also occurred. In addition, douching is time consuming and messy.

External scented sanitary napkins also present problems. They may bulge, bunch up, and require the wearing of belts, straps and pins. They may also slip. They are difficult to store and require proper disposal once used. Motion of the napkin may cause irritation and chafing of the inner thigh and vulva. The properties of the scent may be lost once the napkin is saturated. The external pads of U.S. Pat. Nos. 3,037,506 and 3,690,321 are subject to at least some of these problems.

Tampons which incorporate a scent in the tampon body (the cylindrical plug of absorbent material) present the following disadvantages: First, the scent is provided internally within the vaginal cavity and not at the vulva which is exposed to the environmental air where odors become apparent. Secondly, by having the scent-providing substance in the tampon body inside the vagina, the substance may cause local irritation and sensitivity reactions of the vagina. Also in this position there is the increased possibility of absorption of the substance through the membranes of the vagina causing effects as stated above. The catamenial devices disclosed in U.S. Pat. Nos. 3,690,321, 3,815,600 and 3,830,237 are subject to these disadvantages, as are those devices in which a deodorized pad contacts the vaginal entrance. Similar problems would occur if the principle of medicating suppositories (see U.S. Pat. No. 3,777,755) were applied to vaginal tampons.

The art is therefore moving in the direction of expensive and bulky tampons, such as those shown in U.S. Pat. No. 3,791,385. However, even if these efforts were able to stop an escape of offensive substances, they still would not solve the problem of vulvar odors.

Use in the vulvar region of trinkets or perfumed jewelry of the type shown in U.S. Pat. Nos. 1,683,545, 2,109,092 and 3,270,525 would lead to discomfort and injury.

In some instances the last tampon used is forgotten and not removed, or a second tampon is inserted without removing the one previously installed. If the forgotten tampon is not removed, irritation of the vagina may result.

SUMMARY OF THE INVENTION

It is a general object of this invention to overcome the above mentioned disadvantages.

It is a related object of this invention to provide an improved vulvar deodorant system.

It is a germane object of this invention to provide an improved article for deodorizing the female vulva.

It is also an object of this invention to discourage and avoid a direct application of deodorizing substances to the vulva or the vagina.

It is a related object of this invention to avoid occurrences of ill effects that were previously associated with attemps to deodorize the vulvar region or the vagina itself.

It is a further object of this invention to provide a reminder that the vagina has been provided with a tampon. It is another object of this invention to provide females with a means of personal adornment in periods where an encouragement in this sense is helpful.

The invention resides in an article of manufacture for use in a female vagina and vulvar region, comprising in combination a tampon for insertion into the vagina, means for deodorizing the vulvar area comprising means for retaining a deodorant, and a deodorant retained by these retaining means, and elongate means connected to the tampon and to the retaining means for suspending the retaining means and deodorant outside of the vagina and at a distance therefrom, when the tampon is inserted in the vagina.

In a preferred embodiment of the invention, the suspending means include a string or string-like tape or ribbon member connected to the tampon and having a length sufficient to suspend the retaining means and deodorant outside of the vagina and at a distance therefrom.

In accordance with a further preferred embodiment of the subject invention, the retaining means include a carrier for the deodorant attached to the mentioned suspending means or string at a distance from the tampon sufficient for a suspension of the carrier outside of the vagina and at a distance therefrom.

In accordance with a further preferred embodiment of the invention, the mentioned retaining means or carrier may have a flat configuration. By way of example, these retaining means or carrier may be in the form of an adornment. For instance, a floral configuration may be chosen for this purpose.

BRIEF DESCRIPTION OF THE DRAWING

The subject invention and its objects and aspects will become more readily apparent from the following detailed description of preferred embodiments thereof, illustrated by way of exampdle in the accompanying figure of the drawing showing a cross-section through the lower female anatomy and a side view of an installed vaginal deodorant system according to a preferred embodiment of the subject invention.

DESCRIPTION OF PREFERRED EMBODIMENTS

By way of general background, the female anatomy 10 shown in the drawing has a vulva 12 including the labia majora, one of which is apparent at 13, and the vagina entrance 14. The female anatomy 10 also includes the vaginal canal 15 leading from the vulva 12 via the entrance 14 to the uterus 16. The bladder 17 exits through the urinary canal 18. Those skilled in the art will recognize that the illustrated organs are somewhat diagrammatically shown.

The vulvar deodorant system 20 according to the illustrated preferred embodiment of the subject invention comprises the combination of a tampon 21, shown inserted into the vagina or vaginal canal 15, means for deodorizing the vulvar area comprising a tag 23 for retaining a deodorant, and a deodorant retained by that tag, and means, such as a string or string-like member 24, connected to the tampon 21 and to the deodorant retaining tag 23 for suspending that retaining tag and the retained deodorant outside of the vagina or vaginal canal 15 but adjacent thereto, when the tampon 21 inserted into the vagina or the vaginal canal 15 as shown in the drawing.

The string or string-like member 24 connected to the tampon 21 has a length sufficient to suspend the retaining tag and the deodorant outside of the vagina or vaginal canal 15 and at a short distance therefrom.

The tag 23 preferably is of a shape that may be comfortably receivved when suspended between the legs by the string or string-like member 24 at a distance from the vestibule of the vagina. For maximum comfort, the tag 23 preferably has a flat configuration and is of a relative soft material so as to be easily accommodated between the thighs 25 of the wearer.

To enhance the morale of the wearer, such as during the menstrual period or other instances of occasional depression, the tag 23 is preferably in the form of an adornment, the esthetic appearance of which frequently has the desired effect. In particular, the tag 23 may have a floral configuration as shown in the drawing.

The tampon 21 may be a conventional device made of cotton, cellulose wadding or another highly absorbent material. By way of further example, the deodorant suspension means 24 may comprise a preferably moisture-proof string connected or attached to the tampon 21.

The tag 23 may be made of the same material as the tampon 21 or of another carrier for the employed deodorant. Preferably the tag 23 is water resistant. The tag 23 is connected or attached to the string 24.

The deodorant applied to or combined with the tag 23 may be or contain a perfume or a scenting compound or other deodorant of an odor absorbing type. Suitable absorbent materials and scenting compounds are disclosed in U.S. Pat. No. 3,830,237, by Bernardin et al, issued Aug. 20, 1974, and herewith incorporated by reference herein.

In addition to suspending the deodorant tag, the string 24 may also serve as a withdrawing string facilitating a removal of the tampon 21 at the end of its use. The deodorant tag 23, in turn, may moreover perform the function of an indicator or warning sign that a tampon 21 is located in the vaginal canal 15. In this manner, potential mishaps or injuries resulting from a forgotten tampon are minimized.

Since the deodorant retaining tag 23 is suspended outside of and at a distance from the vagina or vaginal canal 15, the above mentioned injurious influences of the deodorant are safely avoided while the vulvar region 12 is effectively deodorized.

It will thus be recognized that the illustrated preferred embodiment comprises a tag 23 conaining or combined with a deodorizing substance. The tag 23 is attached to the string 24 of a vaginal tampon 21. The attachment of the tag 23 to the tampon string 24 is at the point which is exterior to the vagina when the tampon is in place in the vagina 15. With the tampon 21 in place in the vagina 15, the tag 23 is located at the vulva 12. In this position, the deodorizing substance contained in or combined with the tag 23 will be manifested at the vulvar area 12.

While a preferred embodiment of the subject invention has been illustrated, the present extensive disclosure will render apparent or suggest to those skilled in the art various modifications and variations within the spirit and scope of the invention.

In either case the subject invention and its various embodiments overcome the above mentioned prior-art disadvantages and meet the above mentioned objectives. In particular, the articles and techniques according to the invention afford the desired deodorant action to the vulvar region or other parts of the female anatomy. By their benevolent action the articles of the subject invention may uplift the morale of the female wearer. Most importantly, by providing effective deodorizing articles and techniques, the subject invention effectively discourages the use of, and obviates the need for, those harmful deodorizing practices, sprays and the like which by their deleterious action have already aroused the concern of public and private health authorities.

I claim:

1. An article of manufacture for use in a female vagina and vulvar region comprising in combination:
a tampon for insertion into the vagina;
means for deodorizing the vulvar area comprising means for retaining a deodorant, and a deodorant retained by said retaining means; and
means connected to said tampon and to said retaining means for suspending said retaining means and deodorant outside of the vagina and at a distance therefrom, when said tampon is inserted in said vagina.

2. An article as claimed in claim 1, wherein:
said suspending means include a string or string-like member connected to said tampon and having a length sufficient to suspend said retaining means and deodorant outside of the vagina and at a distance therefrom.

3. An article as claimed in claim 2, wherein:
said retaining means include a carrier for said deodorant attached to said string or string-like member at a distance from said tampon sufficient for a suspension of said carrier outside of the vagina and at a distance therefrom.

4. An article as claimed in claim 3, wherein:
said carrier has a flat configuration.

5. An article as claimed in claim 4, wherein:
said carrier is in the form of an adornment.

6. An article as claimed in claim 4, wherein:
said carrier has a floral configuration.

7. An article as claimed in claim 1, wherein:
said retaining means include an carrier for said deodorant attached to said suspending means at a distance from said tampon sufficient for a suspension of said carrier outside of the vagina and at a distance therefrom.

8. An article as claimed in claim 7, wherein:
said carrier has a flat configuration.

9. An article as claimed in claim 8, wherein:
said carrier is in the form of an adornment.

10. An article as claimed in claim 8, wherein:
said carrier has a floral configuration.

11. An article as claimed in claim 1, wherein:
said retaining means have a flat configuration.

12. An article as claimed in claim 11, wherein:
said retaining means are in the form of an adornment.

13. An article as claimed in claim 11, wherein:
said retaining means have a floral configuration.

14. An article as claimed in claim 1, wherein:
said retaining means are in the form of an adornment.

15. An article as claimed in claim 1, wherein:
said retaining means have a floral configuration 16. An article as claimed in claim 1, wherein:
said retaining means is of a soft material.

17. An article as claimed in claim 1, wherein:
said deodorant includes a perfume scent.

* * * * *